(12) United States Patent
Doty

(10) Patent No.: US 7,510,046 B2
(45) Date of Patent: Mar. 31, 2009

(54) LOW ATTENUATING PUSH-IN EARPLUG WITH INTEGRAL HANDLE

(75) Inventor: Marc L. Doty, Brownsburg, IN (US)

(73) Assignee: Cabot Safety Intermediate Corporation, Newark, DE (US)

( * ) Notice: Subject to any disclaimer, the term of this patent is extended or adjusted under 35 U.S.C. 154(b) by 353 days.

(21) Appl. No.: 11/293,642

(22) Filed: Dec. 2, 2005

(65) Prior Publication Data

US 2007/0080018 A1    Apr. 12, 2007

Related U.S. Application Data

(60) Provisional application No. 60/725,586, filed on Oct. 10, 2005.

(51) Int. Cl.
*H04R 25/02* (2006.01)
*A61F 11/08* (2006.01)
*A61F 11/06* (2006.01)

(52) U.S. Cl. ............ 181/135; 181/130; D24/106; 128/867

(58) Field of Classification Search ........... 181/135, 181/130; D24/106, 174, 173; D29/112; 381/324, 380, 68.6, 328, 329, 69; 128/864, 128/867; D14/223
See application file for complete search history.

(56) References Cited

U.S. PATENT DOCUMENTS

| | | | | |
|---|---|---|---|---|
| 2,393,005 | A | | 1/1946 | Veneklasen |
| 2,446,707 | A | * | 8/1948 | Leight ............ 128/864 |
| 2,672,863 | A | * | 3/1954 | Leight ............ 128/867 |
| 2,717,596 | A | * | 9/1955 | Knight ............ 128/867 |
| 2,824,558 | A | * | 2/1958 | Michael et al. ...... 128/865 |
| 3,097,643 | A | * | 7/1963 | Santi ............. 128/867 |
| 3,130,810 | A | * | 4/1964 | Werner ............ 181/135 |
| 3,871,372 | A | * | 3/1975 | Bivins ............ 128/866 |
| 3,881,570 | A | * | 5/1975 | Lewis ............ 181/135 |
| D241,881 | S | * | 10/1976 | Peterson et al. ....... D24/106 |
| 4,089,332 | A | * | 5/1978 | Rose ............. 128/865 |
| 4,193,396 | A | * | 3/1980 | Wacker ........... 128/864 |
| 4,219,018 | A | * | 8/1980 | Draper, Jr. ......... 128/864 |
| 4,253,452 | A | * | 3/1981 | Powers et al. ....... 128/864 |
| 4,314,553 | A | * | 2/1982 | Westerdal ......... 128/864 |

(Continued)

FOREIGN PATENT DOCUMENTS

EP    1 498 092    1/2005

(Continued)

OTHER PUBLICATIONS

International Search Report; PCT/US2006/039642; Jun. 28, 2007.

*Primary Examiner*—Edgardo San Martin
(74) *Attorney, Agent, or Firm*—Cantor Colburn LLP

(57) ABSTRACT

The invention provides an earplug and a method of forming thereof where the earplug includes an insertion portion having opposing top and bottom sides, a handle portion connected to and extending rearwardly from the bottom of the insertion portion, and a rear portion extending from the top of the insertion portion to the handle portion, where the insertion portion is configured to be partially inserted into an ear canal of a wearer, where the handle portion remains at least partially extending from the ear canal for use in handling the earplug, and where the insertion portion and the handle portion are integrally formed of a resilient compressible material.

24 Claims, 3 Drawing Sheets

U.S. PATENT DOCUMENTS

| | | | | |
|---|---|---|---|---|
| 4,552,137 A | * | 11/1985 | Strauss | 128/864 |
| 4,564,009 A | * | 1/1986 | Brinkhoff | 128/864 |
| 4,806,186 A | | 2/1989 | Sirkin et al. | |
| 4,867,149 A | * | 9/1989 | Falco | 128/864 |
| 4,916,758 A | * | 4/1990 | Jordan-Ross | 2/174 |
| 5,074,375 A | * | 12/1991 | Grozil | 181/135 |
| 5,188,123 A | * | 2/1993 | Gardner, Jr. | 128/864 |
| 5,573,015 A | * | 11/1996 | Williams | 128/864 |
| 5,996,584 A | * | 12/1999 | Oliveira et al. | 128/864 |
| D424,697 S | * | 5/2000 | Fretz et al. | D24/174 |
| 6,105,715 A | * | 8/2000 | Knauer | 181/135 |
| 6,179,085 B1 | * | 1/2001 | Brimhall et al. | 181/135 |
| D452,909 S | * | 1/2002 | Saulce | D24/106 |
| 6,830,124 B2 | * | 12/2004 | Chiang | 181/135 |
| 6,938,621 B1 | | 9/2005 | Greenhaw et al. | |
| D538,924 S | * | 3/2007 | Doty | D24/106 |
| 7,185,655 B1 | * | 3/2007 | Redon | 128/864 |
| 2003/0029460 A1 | * | 2/2003 | Tiemens | 128/864 |
| 2005/0039761 A1 | | 2/2005 | Jenkins | |
| 2005/0056288 A1 | | 3/2005 | Schreiber | |
| 2007/0227546 A1 | * | 10/2007 | Schumaier | 128/864 |

FOREIGN PATENT DOCUMENTS

| | | |
|---|---|---|
| FR | 2 773 988 | 7/1999 |
| WO | 03/037235 | 5/2003 |
| WO | 2005/063155 | 7/2005 |

* cited by examiner

LOW ATTENUATING PUSH-IN EARPLUG WITH INTEGRAL HANDLE

CROSS REFERENCE TO RELATED APPLICATION

This application is related to and claims the benefit of U.S. Provisional Application No. 60/725,586 filed on Oct. 10, 2005, the entire contents of which are incorporated by reference herein.

TECHNICAL FIELD OF INVENTION

The invention concerns hearing protection devices and, more particularly, a push-in or minimally rolled down type earplug with an integral handle that provides a reduced attenuation.

BACKGROUND OF INVENTION

Hearing protection devices, such as earplugs, are readily used to provide sound attenuation. Earplugs include any of a variety of devices designed to be inserted in the ear canal of a user and worn therein to prevent sounds from entering. Generally, there are two types of earplugs: push-in earplugs and roll-down earplugs.

Push-in type earplugs generally comprise an attenuating portion and a rigid or semi-rigid portion typically extending therefrom or embedded therein. The sound attenuating portion is typically of a soft compressible material; the rigid or semi-rigid portion may be composed of any material, such as a plastic or a rubber, with sufficient rigidity as required.

To insert the push-in type earplug, the user grasps the rigid/semi-rigid portion (or an end of the earplug proximate thereto), positions the earplug proximate the ear canal opening, and inserts the sound attenuating portion into the canal by pushing with the rigid/semi-rigid portion. The sound attenuating portion compresses, as necessary, upon entry into the ear canal and is held therein by a friction fit, occluding the canal and providing sound attenuation. Such a push-in type earplug may be found, for example, in U.S. Pat. Nos. 4,867,149 and 5,188,123 to Falco and Gardner Jr., respectively, which are herein incorporated by reference in their entirety.

These known push-in type earplugs have been found to be effective at attenuating sound and thus providing sufficient hearing protection to the wearer. For example, such earplugs, when properly inserted have been shown to provide a Single Number Rating (hereinafter, "SNR") often greater than 25. However, sometimes a relatively lower level of sound attenuation is desired. For example, an earplug wearer in a low-noise environment may desire an SNR of approximately 20 or lower. Such reduced SNR would provide the wearer with sufficient attenuation while allowing certain sounds, such as nearby conversation, to penetrate the ear. The push-in earplug would likely provide to much attenuation to allow such desirable sounds to be audible. Also, certain discomforts are typically associated with this type of push-in earplug as a result of the presence of the rigid or semi-rigid stem portion. Further, manufacture of the push-in earplug may be complicated and relatively expensive in that the attenuating portion and the rigid or semi-rigid portion may be required to be formed separately and then later affixed together.

A roll-down type earplug includes an attenuating portion similar to that of the push-in but does not include the rigid or semi-rigid portion. Instead, insertion is facilitated by rolling down the earplug into a compressed state having a reduced diameter which enables the earplug to be passed into the earcanal wherein the earplug expands to occlude the canal. A typical roll-down earplug may be found in U.S. Pat. No. 6,105,715 to Knauer which is herein incorporated by reference in its entirety.

As with push-in type earplugs, roll-down plugs attenuate sound by causing an occlusion deep within the earcanal, thus obstructing the passage of sound therethrough. However, the required insertion method is slightly more complex, requiring a precise roll-down of the plug and a manipulation of the pinna portion of the ear during ear canal insertion. See, U.S. patent application Ser. No. 10/740,180 filed on Dec. 17, 2003, which is herein incorporated by reference in its entirety.

Errors during insertion of roll-down earplugs result in improper fit within the earcanal, and thus full occlusion may not be achieved. For example, the earplug may be rolled down properly, but only inserted partially into the earcanal. Thus, the surface area of the plug in contact with the earcanal walls is reduced, full occlusion is not attained, and attenuation is degraded. Further, the earplug may be mis-handled during pre-insertion roll-down preparations. For example, the plug may improperly rolled and/or compressed prior to insertion such that creases are formed on the surface of the plug. These creases act as sound channels and permit the leakage of sound into the canal, thus degrading occlusion, and effecting attenuation.

These roll-down earplugs provide a degree of comfort to the wearer but are often regarded as complicated to properly insert into the ear canal. Additionally, once inserted, such roll-down earplugs typically provide a high SNR (e.g., 30 or higher). Thus, these roll-down earplugs may not be effective in a low noise situation where a reduced SNR is desired.

Partial insertion of either the push-in type or roll-down type earplugs may provide a lesser SNR than such earplugs provide when fully and properly inserted. However, it would be extremely difficult to attain a consistent reduced SNR in this manner because the slightest deviation in partially inserting one earplug over another would increase or decrease the attenuation provided thereby. Moreover, there is no way that a user could accurately know the protection provided by a partially inserted traditional push-in or roll-down earplug. Thus, in attempting such partial insertion a wearer may inadvertently reduce the SNR far too much thus exposing the inner ear to damaging noise.

Accordingly, an earplug is desired which is inserted simply and effectively, and which is comfortable to the wearer, and which provides a consistent relatively lower sound attenuation than traditional push-in and roll-down earplugs.

BRIEF SUMMARY OF THE INVENTION

The above discussed and other problems and deficiencies of the prior art are overcome or alleviated by the invention which provides a novel and nonobvious hearing protection device.

The invention provides an earplug including a substantially semi-hemispherical insertion portion having opposing top and bottom sides, a handle portion connected to and extending rearwardly from the bottom of the insertion portion, and a rear portion extending from the top of the insertion portion to the handle portion, where the insertion portion is configured to be partially inserted into an ear canal of a wearer, and where the insertion portion and the handle portion are integrally formed of a resilient compressible material.

In another embodiment, the invention provides an earplug including a front insertion portion, a single rear flange extending from a periphery of the front insertion portion in a direction away from the insertion portion, a push-in portion delimited by the intersection of the front insertion portion and the single rear flange, where the front insertion portion is configured to be partially inserted into an ear canal of a wearer, and where the front insertion portion and the single rear flange are integrally formed of a resilient compressible material.

The invention also provides a method of manufacturing an earplug including forming an earplug blank having a generally cylindrical shape and severing the earplug blank at an angle to a longitudinal axis of the earplug blank to form at least one earplug having a cylindrical insertion portion and a truncated cylindrical handle portion.

The invention further provides a method of manufacturing a plurality of earplugs including forming an earplug blank having a generally elongated cylindrical shape and severing the earplug blank alternately at approximately 45° to a longitudinal axis of the earplug blank and at approximately 90° to the longitudinal axis to form the plurality of earplugs, each of the earplugs having a cylindrical insertion portion and a truncated cylindrical handle portion.

The above-discussed and other features and advantages of the apparatus and method of the invention will be appreciated and understood by those skilled in the art from the following drawings and detailed description.

BRIEF DESCRIPTION OF THE FIGURES

Referring now to the drawings wherein like elements are numbered alike in the several FIGURES.

DETAILED DESCRIPTION OF THE PREFERED EMBODIMENT

Figure 1:
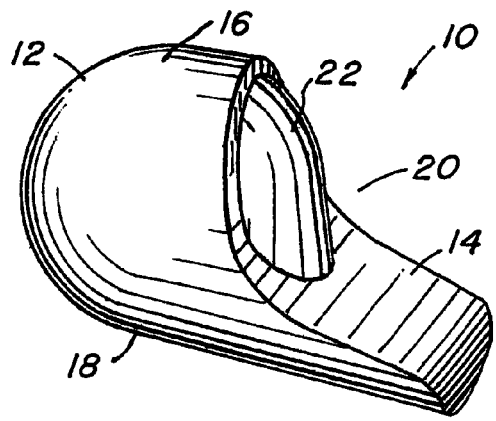
FIG. 1 is a perspective view of an earplug in one embodiment of the invention.

FIGS. 1-6 show an earplug 10 in one exemplary embodiment of the invention. The earplug includes an insertion portion 12 and a handle portion 14. The insertion portion 12 is shaped and sized to facilitate entry and retention of the earplug 10 within an ear canal of a wearer. That is, the insertion portion 12 is generally semi-hemispherical in shape and is sized to have a diameter slightly larger than an average ear-canal such that, upon insertion into the canal, the insertion portion 12 is slightly compressed into a friction fit within the canal. The insertion portion 12 includes a top portion 16 which extends in a rearward direction toward the handle portion 14. The top 16 of the insertion portion 12 extends for generally half of a longitudinal length of the earplug 10, as can be best seen in FIG. 2. The insertion portion 16 further includes a bottom 18 disposed opposite from the top 16. The bottom 18 of the insertion portion 12 extends rearwardly toward the handle portion 14. In fact, the bottom of the insertion portion meets the handle portion 14 as shown in the drawings.

Figure 3:
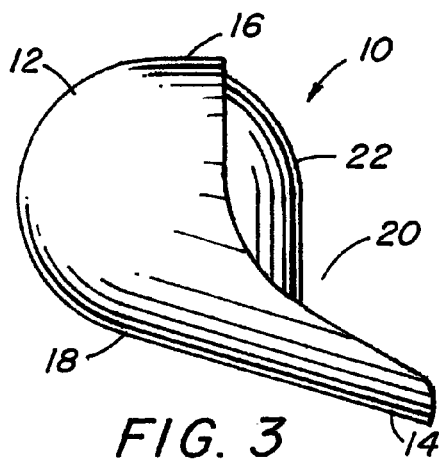
FIG. 3 is a side elevation view thereof.
Figure 4:
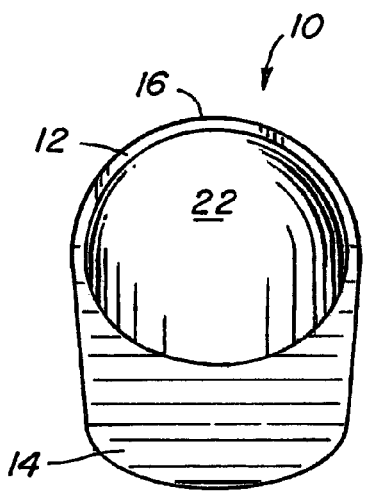
FIG. 4 is a front view thereof.
Figure 5:
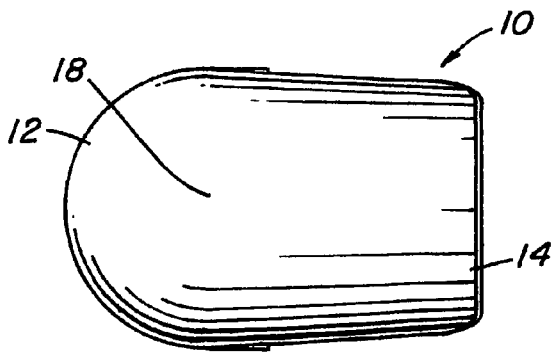
FIG. 5 is a bottom view thereof.
Figure 6:
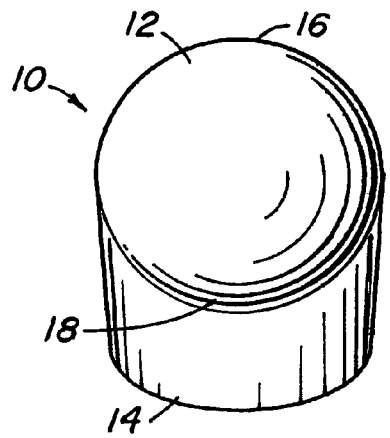
FIG. 6 is a rear view thereof.

The handle portion 14 of the earplug 10 extends from the bottom 18 of the insertion portion 14. The handle portion 14 is essentially a wing-like flange which tapers in the rearward direction away from the insertion portion 12. Notably, the handle 14 generally extends only from one side of the insertion portion 12. That is, the handle 14 extends from the bottom 18 of the insertion portion 12 while the top 16 of the insertion portion 12 terminates at an approximate mid-point of the longitudinal length of the earplug 10, as mentioned above. This configuration creates a large cavity at the rear of the earplug 10 above the handle 14. The cavity is generally indicated in FIGS. 1 and 3 by the reference numeral 20.

Figure 2:
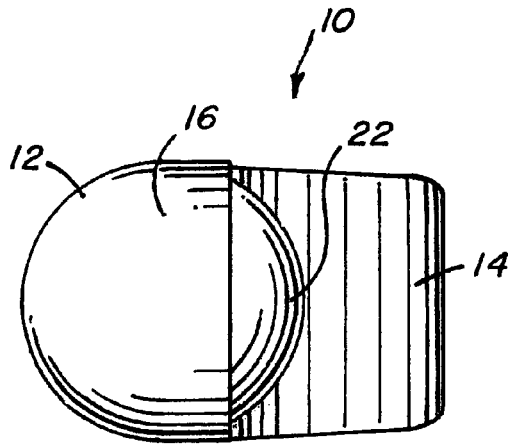
FIG. 2 is a top plan view thereof.

The earplug 10 further includes a rear portion 22 disposed in the cavity 20. The rear portion 22 extends generally from the top 16 of the insertion portion 12 to the handle 14. The rear portion 22 is substantially semi-hemispherical in shape and projects slightly in the rearward direction from the insertion portion 12, as best seen in FIGS. 1-3.

The earplug 10 is preferably composed of a compressible resilient, slow recovery thermoplastic foam material. The earplug 10 may be manufactured in a molding process as is conventionally known in the art.

In use, the wearer may grasp the earplug 10 by the handle 14 and place the insertion portion at the entrance of the ear canal. Then the wearer may place a tip of a finger in the cavity 20 against the rear portion 22 where the rear portion 22 meets the handle 14. This area of the earplug is naturally receptive to the finger tip. That is, the contouring of this part of the earplug 10 receives and tends to retain the finger tip during insertion of the earplug 10. Once the finger tip is in place as described, pressure may be applied therewith to the rear portion 22 of the earplug 10. This pressure eases the insertion portion 12 into the ear canal. The shape and size of the insertion portion 12 allows partial insertion thereof into the ear canal. That is, the insertion portion 12 essentially caps the ear canal with part of the insertion portion 12 lodged therein and part extending rearwardly therefrom. When the earplug 10 is properly inserted, the handle portion 14 remains extending entirely from the ear canal adjacent to the pinna of the ear. Thus, the handle portion remains available for the wearer to grasp and remove the earplug 10 from the canal when desired by gently pulling outward thereon.

As mentioned, when properly inserted the earplug 10 lies only partially within the ear canal, thus serving to cap the entrance of the canal and to provide the desired occlusion. This capping results in a reduced attenuation rating of approximately SNR 15 to SNR 25. More particularly an attenuation rate of SNR 21 is generally provided by the earplug 10.

Additionally, the earplug 10 is simple to insert. This is because no specific roll-down procedure is required. The wearer simply places a finger tip at the rear portion 22 of the earplug 10 and presses the insertion portion 12 into the ear canal, as discussed above. Moreover, the earplug 10 provides a high degree of comfort to the wearer. This is because the earplug 10 includes no rigid or semi-rigid insert, as is common in push-in earplugs. Comfort is also provided because the earplug 10 is only partially inserted into the earcanal, unlike roll-down earplugs which are fully inserted in a compressed state and then allowed to expand therein against the walls of the ear canal. Further comfort is provided during insertion of the earplug 10 because the rear portion 22 of the earplug 10 is configured to yield slightly in response to the pressure applied by the wearer's finger tip. In this way, a sudden pressure (i.e., a poking, etc.) to the ear may be minimized. Instead, the earplug 10 simply eases naturally into the ear canal.

It has been described thus far that the earplug 10 is inserted by a simple push-in method. However, wearer's with smaller than average ear canal diameters may chose to slightly roll-down the earplug 10 to reduce the diameter thereof, thus facilitating insertion of the earplug 10 into the ear canal. For example, the earplug 10 may be rolled gently between thumb and forefinger to compress the earplug 10 slightly. Similarly, the earplug 10 may be rolled between the palms of the hands or between one hand and a flat surface such as a table. Any of these simple techniques temporarily reduces the cross-sectional diameter of the earplug 10, and particularly, of the insertion portion 12. In this rolled-down state, the wearer inserts the earplug 10 as described above. That is, the insertion portion 12 is placed at the entrance of the ear canal and a tip of the finger is pressed at the rear portion 22 of the earplug such that the insertion portion 12 slips partially into the ear canal. Within moments, the compressible resilient material of the insertion portion 12 regains it's original, uncompressed diameter within the ear canal thus gently securing the earplug 10 therein.

Notably, the handle portion 14 of the earplug 10 is formed integrally with the insertion portion 12. No separate manufacturing of the handle is required, nor is assembly of the insertion portion 12 and the handle 14 necessary. The insertion portion 12 and the handle portion 14 are formed simultaneously and integrally of the same material, preferably a foamed thermoplastic.

As mentioned, the earplug 10 is preferably formed of a compressible, resilient slow recovery foam. Particularly, the earplug may be formed of a thermoset material or a hi-pol-based polyurethane material. Specifically, a foam sold under the tradename "EARform" may be utilized in forming the earplug 10. However, the earplug 10 may be formed of any material having the compressible resilient properties required for insertion and occlusion of the ear canal.

The shape and relative dimensions of the earplug 10 are shown in FIGS. 1-6 by way of example only. The dimensions and/or shape of the earplug 10 and its various parts may be altered as desired. For example, the handle portion 14 may be formed rectilinear in shape or may extend from the top 16 of the insertion portion 12 instead of from the bottom portion, etc.

Figure 7:
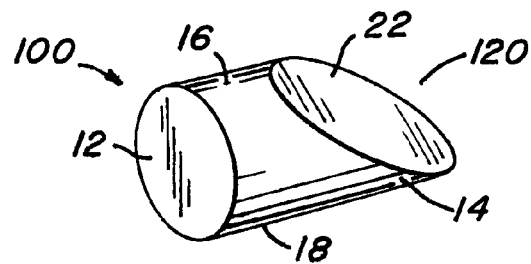
FIG. 7 is a perspective view of an earplug in another embodiment of the invention.
Figure 8:
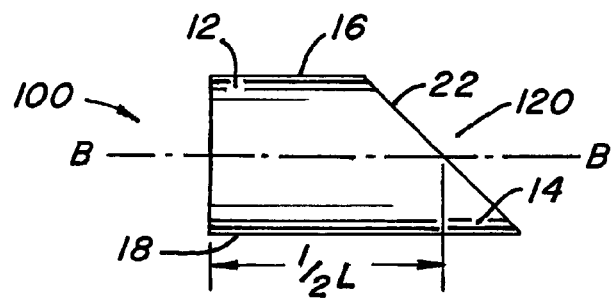
FIG. 8 is a side elevation view thereof.
Figure 9:
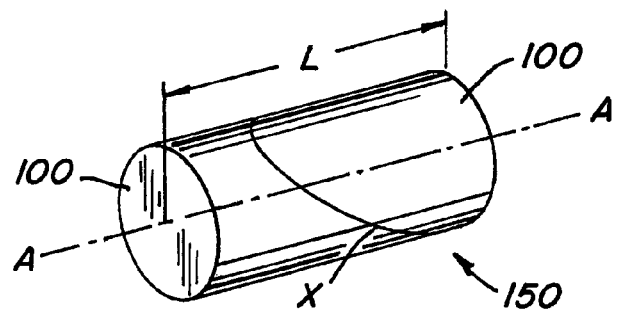
FIG. 9 is a perspective view of a blank from which the earplug of FIG. 7 is manufactured.

In this respect, FIGS. 7-9 show an earplug 100 in another embodiment of the invention. The earplug 100 includes many of the same features and benefits of the earplug 10. Elements which are consistent between the earplugs 10 and 100 are herein indicated by consistent reference numerals and, for sake of brevity, are not re-introduced or discussed in detail.

The earplug 100 is essentially comprises a truncated cylindrical shape and includes the insertion portion 12 and the handle portion 14 disposed at opposite ends of the earplug 100. The insertion portion 12 comprises a generally cylindrical portion of the earplug 100 while the handle portion includes the truncated portion of the earplug 100. Here, the top 16 of the insertion portion 12 extends rearwardly toward the handle portion 14. The bottom 18 of the insertion portion 12 extends rearwardly and meets the handle portion 14, as shown in the drawings. The rear portion 22 of the earplug 100 extends from the top 16 of the insertion portion 12 at an angle downwardly to the handle portion 14. Here, the rear portion 22 is essentially a planar surface which delimits the truncated cylindrical shape of the earplug 100.

Due to its unique shape, the earplug 100 includes a space 120 adjacent to the rear portion 22. This space 22 is receptive to a finger of a wearer when inserting the earplug 100 into the ear canal. That is, the handle portion 14 serves as a handle when the wearer is manipulating the earplug and locating it in the earcanal. Once the earplug 100 is generally positioned at the opening of the earcanal, the wearer may then place a fingertip in the space 20 at the rear portion 22 and press there against to push the insertion portion 12 of the of the earplug 100 into the ear canal.

Similar to the previously discussed embodiment, the earplug 100 is configured for partial insertion within the earcanal. That is, when properly inserted at least some of the insertion portion 12 lies within the earcanal and at least some of the handle portion 14 extends therefrom. In this way, a reduced attenuation is provided of approximately SNR 15 to SNR 25 and preferably about SNR 21. Also, when the earplug 100 is inserted as such, at least part of the handle portion 14 remains extending from the canal and thus is available as a handle by which the wearer may grasp, manipulate, and/or remove the earplug 100 from the earcanal.

The earplug 100 may be sized as discussed above regarding the earplug 10 so as to be slightly larger than the cross-sectional area of the earcanal to thus allow a push-in fiction fit and/or a slight roll-down insertion fit. Also, the earplug 100 may be formed in a molding process of the same compressible, resilient slow recovery material, as discussed above with respect to the earplug 10. Of course, the general shape of the earplug 100 may be varied as desired through such molding process. For example, the insertion end 12 of the earplug 100 may be molded to be slightly rounded as seen in the earplug 10, or it may be made conical, etc.

Figure 10:
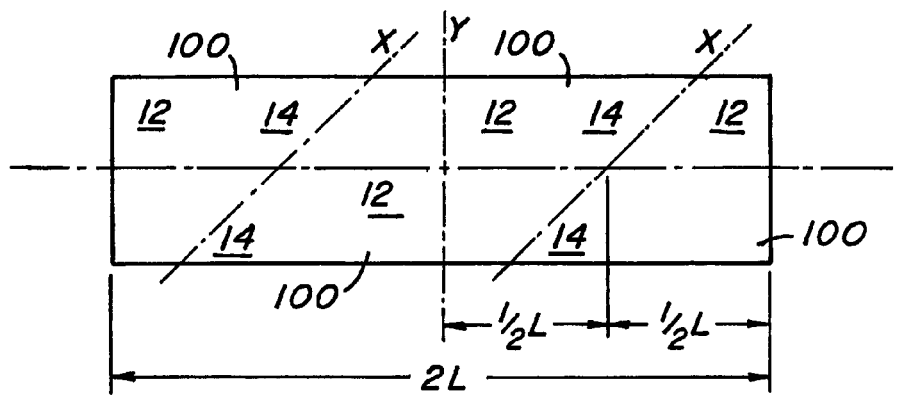
FIG. 10 is a elevation view of a blank in another embodiment of the invention.

In an alternative method of manufacture, the earplug 100 may be formed from a blank 150 as shown in FIG. 9. The blank 150 comprises a cylinder of any desired compressible, resilient material such as, for example, that disclosed in U.S. Reissue Pat. No. 29,487 to Gardner Jr. granted on Dec. 6, 1977, the contents of which are herein incorporated by reference in their entirety. The earplug blank 150 may be formed by any conventional method including, but not limited to, a casting and die-cutting process, a molding process, an extrusion process, etc. The cylinder includes a cross-sectional area identical to that of the earplug 100 and further includes a longitudinal length L which is preferably a multiple of a longitudinal length of the earplug 100. Herein, "longitudinal length" is intended to mean a length measured along longitudinal axes of the respective earplug blank 150 and the earplug 100. As shown in FIG. 8, the longitudinal axis of the earplug 100 is indicated by a line B-B. In FIGS. 9-10, the longitudinal axis of the earplug blank 150 is indicated by a line A-A. In the present exemplary embodiment of FIG. 9, the longitudinal length L of the earplug blank 150 is twice the longitudinal length of the earplug 100. That is, the earplug 100 includes a longitudinal length of ½ L, as shown in FIG. 8. The blank 150 is severed at an angle along the line X of FIG. 9. The line X extends preferably at an angle of 45° relative to a longitudinal axis of the blank 150. The blank 150 may be severed by any sufficient cutting technique including, but not limited to, mechanical cutting, laser cutting, water jet cutting, etc. Severing the blank 150 along line X yields two of the earplugs 100.

Of course, the blank 150 may include a longer longitudinal length such that additional cuts thereof yield additional earplugs 100. For example, as shown in FIG. 10, the blank 150 may include a longitudinal length equal to 2 L. Such a blank may be cut along the two lines X and along a line Y, as shown in the drawing, to yield four earplugs 100. The line Y is generally perpendicular to the longitudinal axis A-A. Severing the blank 150 along the line Y delimits the cylindrical insertion portions 12 of the two respective adjacent earplugs 100. Severing the blank 150 along the lines X delimits the handle portions 14 of the respective adjacent earplugs 100. Of course, the blank 150 may include a length of 4L, 10L, 20L, etc., and thus yield corresponding additional earplugs 100. Essentially, the earplug blank 150 may be of continuous length whereby the blank 150 is then severed as desired to produce a plurality of the earplugs 100. This is particularly relevant in an embodiment where the blank 150 is formed by extrusion, but of course also applies with respect to other manufacturing methods. Accordingly, this method of manufacture provides a low-cost, simple process for forming a plurality of the earplugs 100.

The earplugs 10 and 100 may further include surface treatments as desired. For example, the earplugs 10 and 100 may include text, symbols, coloring, surface texture, surface contour, surface coating, etc., as is desired.

The earplugs 10 and 100 may further include a cord attached thereto. That is, in another embodiment of the invention, a pair of the earplugs 10 or a pair of the earplugs 100 may be connected to one another by way of a cord. The cord is affixed to the individual earplugs 10 and 100 at their respective handle portions 14 or rear portions 22 in a manner so as not to interfere with the handling functions of the handle portion 14 nor with the push-in insertion functions of the rear portions 22, said functions being discussed hereinabove. Such cord may be attached to the earplugs 10, 100 by any suitable means including, but not limited to, adhesive bonding, mechanical bonding, etc. The cord itself may be elastic or non-elastic in nature and may be similar to that described in any of U.S. Pat. No. 5,074,375 to Grozil, U.S. Pat. No. 4,916,758 to Jordan-Ross, U.S. Pat. No. 4,314,553 to Westerdal, U.S. Pat. No. 4,253,452 to Powers et al., U.S. Pat. No. 4,219,018 to Draper, Jr., U.S. Pat. No. 4,193,396 to Wacker, and U.S. Pat. No. 3,871,372 to Bivins, all of which patents are herein incorporated by reference in their entirety. Typically, the cord is a relatively long, continuous and flexible material fixed to, and extending between, the earplugs 10, 100. The cord is of sufficient length, generally ranging from between 21 inches to 27 inches, to extend from one ear to the other ear of a wearer while further providing enough slack to secure the cord to some convenient portion of the wearer's apparel, e.g. a shirt collar, or to be draped around the neck of a wearer when not in use. Suitable materials for such cords are conventional in nature and include natural and synthetic materials, for example, cotton, wool, plastic, plastic such as polyvinylchloride, and may be in the form of a continuous solid strand or a braided/twisted multi-strand construction.

Figure 11:
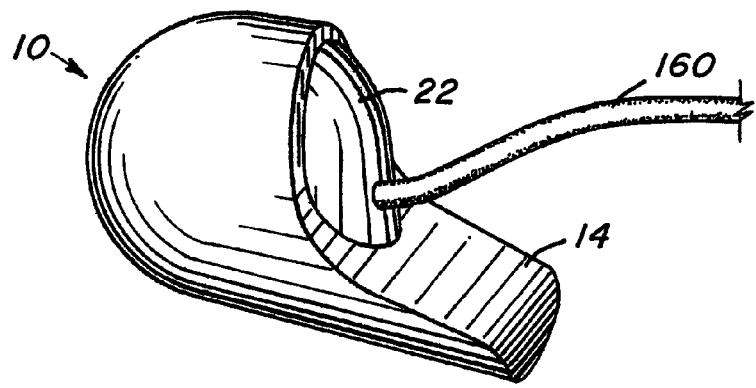
FIGS. 11 and 12 show the earplugs of FIGS. 1 and 7 having a cord attached thereto.
Figure 12:
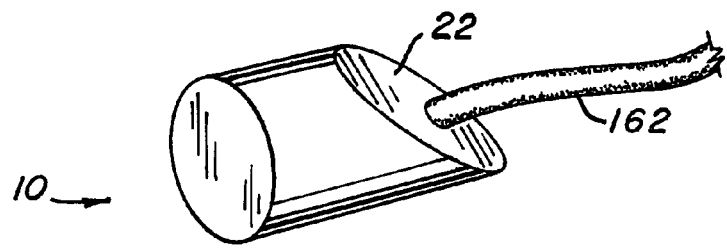

FIG. 11 is an exemplary perspective view of the earplug 10 including a cord 160 attached at the rear portion 22 of the earplug 10. FIG. 12 is a perspective view of the earplug 100 with a cord 162 attached to the rear portion 22 of the earplug 100. The cords 160, 162 are composed and attached as discussed immediately above. Each of the cords 160 and 162 extend away from the earplugs 10 and 100 and are attached to a second respective earplug 10 and 100 (not shown) to thus form a corded pair of earplugs 10 and a corded pair of earplugs 100. The cords 160, 162 are shown by way of example as being fixed at the rear portions 22 of the respective earplugs 10, 100. Of course, the cords 160, 162 may be affixed to the earplugs 10, 100 at any desirable location. For example, the cord 160 may be attached to the handle portion 14 of the earplug 10. Particularly, the cord 160 may be attached at the rearmost end of the handle portion 14, opposite from the insertion portion. The ends of the cords 160 and 162 which attach to the respective earplugs 10 and 100 may simply contact the outer surface of the earplugs or may extend into an interior of the earplugs, as desired.

Thus, as described herein, the invention provides an earplug which yields a reduced sound attenuation and which is easy to handle, simple to insert into the ear canal, and comfortable to wear.

It will be apparent to those skilled in the art that, while exemplary embodiments have been shown and described, various modifications and variations can be made to the present apparatus and method disclosed herein without departing from the spirit or scope of the invention. Accordingly, it is to be understood that the various embodiments have been described by way of illustration and not limitation.

The invention claimed is:

1. An earplug, comprising:
   a substantially semi-hemispherical insertion portion having opposing top and bottom sides;
   a handle portion connected to and extending rearwardly from the bottom of the insertion portion;
   a cavity defined by an expanse between the top of the insertion portion and the handle portion; and
   a rear portion disposed in the cavity, the rear portion including a rearwardly facing convex surface that is distinct from the insertion portion and extends rearwardly away from the insertion portion;
   wherein the insertion portion is configured to be partially inserted into an ear canal of a wearer; and
   wherein the insertion portion and the handle portion are integrally formed of a resilient compressible material.

2. The earplug of claim 1, wherein the resilient compressible material is a foamed thermoset material.

3. The earplug of claim 1, wherein the rear portion and the an intersection of the rear portion and the handle portion are configured to receive and retain a tip of a finger of the wearer to facilitate partial insertion of the insertion portion into the ear canal.

4. The earplug of claim 1, wherein the rear portion extends from the top of the insertion portion to the handle portion in a direction substantially perpendicular to a direction of extension of the handle portion.

5. The earplug of claim 1, wherein the handle portion comprises a single flange extending freely away from the bottom of the insertion portion.

6. The earplug of claim 1, wherein the earplug provides a relatively reduced attenuation rating of approximately SNR 15 to SNR 25.

7. The earplug of claim 1, wherein the earplug provides a relatively reduced attenuation rating of approximately SNR 21.

8. An earplug, comprising:
   a front insertion portion;
   a single rear flange extending from a periphery of the front insertion portion in a direction away from the insertion portion;
   a push-in portion delimited by the intersection of the front insertion portion and the single rear flange, the push-in portion including a constant angle from an upper extent of the front insertion portion to a lower extent of the single rear flange;
   wherein the front insertion portion is configured to be partially inserted into an ear canal of a wearer; and
   wherein the front insertion portion and the single rear flange are integrally formed of a resilient compressible material.

9. The earplug of claim 8, wherein the front insertion portion is substantially semi-hemispherical in shape and wherein the single rear flange extends from the front insertion portion at a bottom side of the periphery.

10. The earplug of claim 8, wherein the push-in portion is configured to receive and retain a tip of a finger of the wearer to facilitate partial insertion of the insertion portion into the ear canal.

11. The earplug of claim 8, wherein the resilient compressible material is a foamed thermoset material.

12. The earplug of claim 8, wherein the earplug provides a relatively reduced attenuation rating of approximately SNR 15 to SNR 25.

13. The earplug of claim 8, wherein the earplug provides a relatively reduced attenuation rating of approximately SNR 21.

14. The earplug of claim 8, wherein the front insertion portion comprises a cylinder and wherein the single rear flange and the push-in portion form a truncated cylinder.

15. The earplug of claim 14 wherein the truncated cylinder is truncated at approximately 45° relative to a longitudinal axis of the earplug.

16. The earplug of claim 14, wherein the insertion portion includes a front end comprising a planar circular surface.

17. The earplug of claim 14, wherein the insertion portion includes a front end comprising a semi-hemispherical surface.

18. The earplug of claim 8, wherein the push-in portion comprises a planar surface disposed at an angle of approximately 45° relative to a longitudinal axis of the earplug.

19. The earplug of claim 8, further comprising a cord having an end attached to the single rear flange or to the push-in portion.

20. A method of manufacturing an earplug, comprising:
    forming an earplug blank having a generally cylindrical shape; and
    severing the earplug blank at an angle to a longitudinal axis of the earplug blank to form at least one earplug having a cylindrical insertion portion at a first end and a truncated cylindrical handle portion at a second end, wherein the second end includes a constant angle from an upper extent of the second end to a lower extent of the truncated cylindrical handle portion.

21. The method of claim 20, wherein the earplug blank has a length approximately twice a longitudinal length of the earplug and wherein the earplug blank is severed at an angle of approximately 45° to the longitudinal axis to form two of said earplugs, each earplug including the cylindrical insertion portion and the truncated cylindrical handle portion.

22. The method of claim 20, wherein the earplug blank has a length greater than approximately twice a longitudinal length of the earplug, the method further comprising severing the earplug blank again at an angle approximately perpendicular to the longitudinal axis and severing the earplug blank again at the angle of approximately 45° to form a plurality of said earplugs, each of said earplugs including the cylindrical insertion portion and the truncated cylindrical handle portion.

23. The method of claim 20, further comprising attaching an end of a cord to the truncated cylindrical handle portion.

24. A method of manufacturing a plurality of earplugs, comprising:
    forming an earplug blank having a generally elongated cylindrical shape; and severing the earplug blank alternately at approximately 45° to a longitudinal axis of the earplug blank and at approximately 90° to the longitudinal axis to form said plurality of earplugs, each said earplug having a cylindrical insertion portion at a first end and a truncated cylindrical handle portion at a second end, wherein the second end includes a constant angle from an upper extent of the second end to a lower extent of the truncated cylindrical handle portion.

* * * * *

UNITED STATES PATENT AND TRADEMARK OFFICE
CERTIFICATE OF CORRECTION

| | |
|---|---|
| PATENT NO. | : 7,510,046 B2 |
| APPLICATION NO. | : 11/293642 |
| DATED | : March 31, 2009 |
| INVENTOR(S) | : Marc L. Doty |

It is certified that error appears in the above-identified patent and that said Letters Patent is hereby corrected as shown below:

<u>Column 8</u>
Line 31, in claim 3, after "and" delete "the".

Signed and Sealed this

Twenty-eighth Day of July, 2009

JOHN DOLL
*Acting Director of the United States Patent and Trademark Office*